(12) United States Patent
Inakoshi et al.

(10) Patent No.: US 7,829,715 B2
(45) Date of Patent: Nov. 9, 2010

(54) METHOD FOR PRODUCING SOLIFENACIN OR SALTS THEREOF

(75) Inventors: Masatoshi Inakoshi, Chuo-ku (JP); Yusuke Ishii, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 986 days.

(21) Appl. No.: 11/587,826

(22) PCT Filed: Apr. 25, 2005

(86) PCT No.: PCT/JP2005/007771

§ 371 (c)(1),
(2), (4) Date: Oct. 27, 2006

(87) PCT Pub. No.: WO2005/105795

PCT Pub. Date: Nov. 10, 2005

(65) Prior Publication Data

US 2007/0185329 A1    Aug. 9, 2007

(30) Foreign Application Priority Data

Apr. 28, 2004  (JP) .................. P.2004-133283

(51) Int. Cl.
   *C07D 453/02*  (2006.01)
(52) U.S. Cl. ....................................... 546/134
(58) Field of Classification Search .............. None
   See application file for complete search history.

(56) References Cited

U.S. PATENT DOCUMENTS 6,017,927 A    1/2000    Takeuchi

FOREIGN PATENT DOCUMENTS

| EP | 0801067 A1 | 10/1997 |
|---|---|---|
| JP | 2002-104968 A | 4/2002 |
| JP | 2003-267977 A | 9/2003 |
| WO | 96/20194 A1 | 7/1996 |
| WO | 03/006019 A1 | 1/2003 |
| WO | 03/031405 A2 | 4/2003 |
| WO | 2008/062282 A2 | 5/2008 |
| WO | 2009/142522 A1 | 11/2009 |

OTHER PUBLICATIONS

Christine E. Heading, Current Opinion in Central & Peripheral Nervous System Investigational Drugs, 2000, pp. 321-325, vol. 2, No. 3 Pharma Press, LTD.
N. Mealy and J. Castaner, Drugs of the Future, Prous Science, 1999, pp. 871-874, vol. 24, No. 8.
Ken Ikeda, Seiji Kobayashi, Mami Suzuki, Keiji Miyata, Makoto Takeuchi, Toshimitsu Yamada, Kazuo Honda, M3 receptor antagonism by the novel antimuscarinic agent solifenacin in the urinary bladder and salivary gland, Naunyn-Schmiedeberg's Arch Pharmacol, 2002, pp. 97-103, vol. 366, No. 2.
Seiji Kobayashi, Ken Ikeda, Mami Suzuki, Toshimitsu Yamada, Keiji Miyata, Effects of YM 905, a Novel Muscarinic M3-Receptor Antagonist, on Experimental Models of Bowel Dysfunction in Vivo, Jpn J. Pharmacol, 2001, pp. 281-288, vol. 86 No. 3.
Supplementary European search report issued on Mar. 29, 2010 in the counterpart European Application No. 05734743.7-2123.
Office Action issued in Canadian Patent Application No. 2,564,757; dated Aug. 11, 2008.
European Office Action issued Jul. 21, 2010 in corresponding European Application No. 05734743.7.

*Primary Examiner*—Zinna N Davis
(74) *Attorney, Agent, or Firm*—Sughrue Mion, PLLC

(57) ABSTRACT

There is provided a novel method for producing solifenacin or a salt thereof which is useful as a medicine, particularly a therapeutic agent and/or a preventive agent for a urinary organ system disease such as pollakiuria or urinary incontinence. Illustratively, there are provided (1) a method for producing solifenacin in which 2-(1H-Imidazolylcarbony1)-1-phenyltetrahydroisoquinoline is used as the starting material, (2) a method for producing solifenacin succinate in which (1RS)-phenyltetrahydroisoquinoline-carboxylic acid quinuclidinyl ester is used as the starting material, (3) a method for producing solifenacin in which a lower alkyl quinuclidinyl carbonate is used as the starting material and (4) a method for producing solifenacin in which phenyltetrahydroisoquinoline-carboxylic acid secondary lower alkyl or tertiary lower alkyl ester is used as the starting material and allowed to react with an alkali metal lower alkoxide.

4 Claims, 4 Drawing Sheets

METHOD FOR PRODUCING SOLIFENACIN OR SALTS THEREOF

Figure 1:
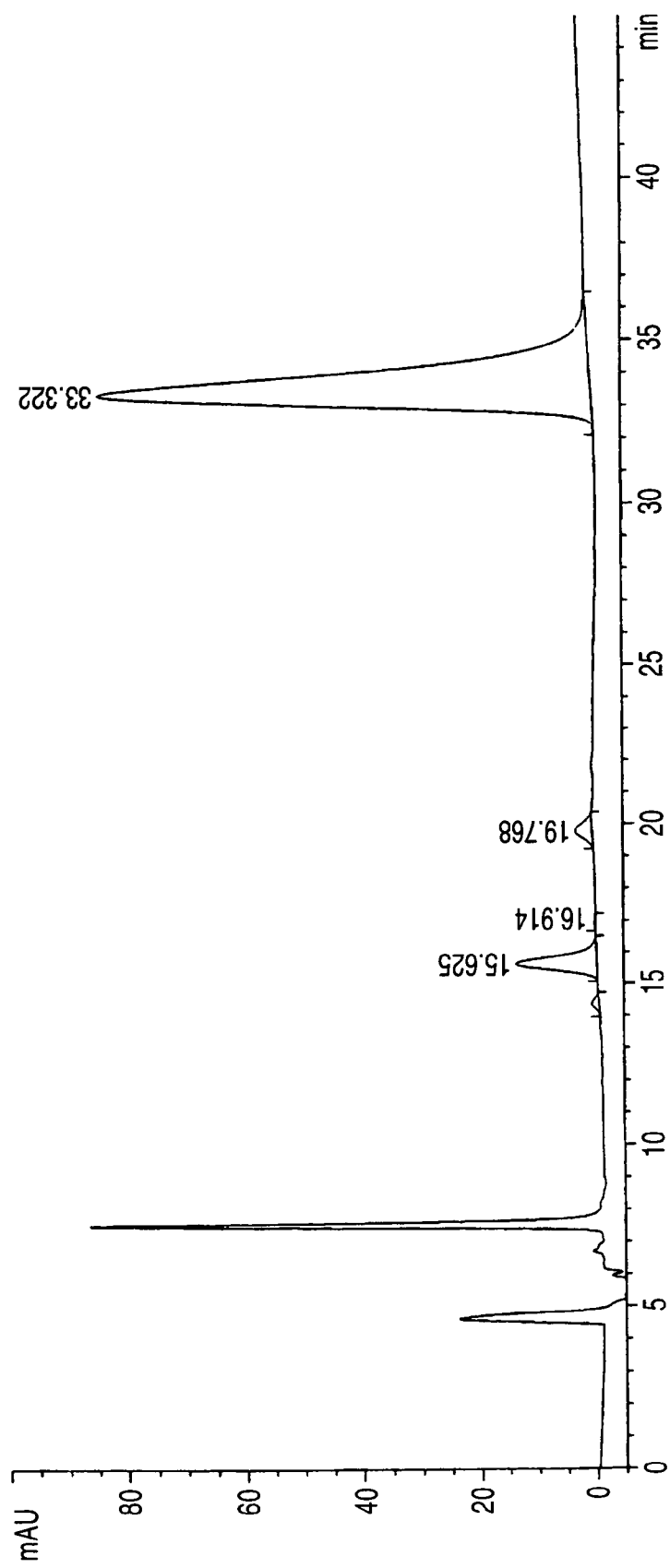

This application is a 371 of PCT/JP05/07771 filed Apr. 25, 2005.

TECHNICAL FIELD

This invention relates to a novel method for producing solifenacin or a salt thereof which is useful as a medicine, particularly a muscarine $M_3$ receptor antagonist, more illustratively a therapeutic agent and/or a preventive agent, for example, a therapeutic agent or the like for a urinary organ disease such as pollakiuria, urinary incontinence or the like accompanied by overactive bladder.

TECHNICAL BACKGROUND

Chemical name of solifenacin is (1S)-1-phenyl-1,2,3,4-tetrahydroisoquinoline-2-carboxylic acid (3R)-quinuclidin-3-yl ester, and it has the following chemical structure.

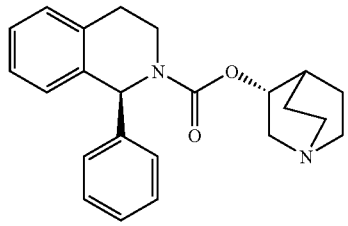

Solifenacin or a salt thereof is a compound known as a muscarine $M_3$ receptor antagonist (Patent Reference 1, Non-patent Reference 1, Non-patent Reference 2, Non-patent Reference 3) and is on the market as a therapeutic agent for pollakiuria and urinary incontinence accompanied by overactive bladder. In addition, its usefulness for interstitial cystitis (Patent Reference 2), tension alleviation of ciliary muscle (Patent Reference 3), irritable bowel syndrome (Non-patent Reference 4) and the like has also been reported.

Regarding solifenacin or a salt thereof, the following production method X and production method Y are specifically known (Patent Reference 1).

(a) Production Method X

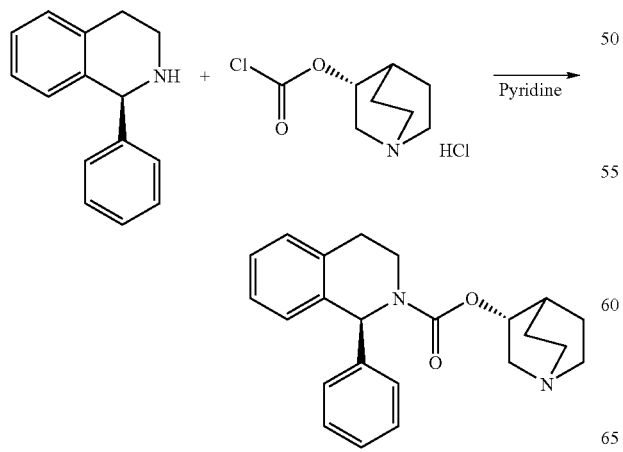

(b) Production Method Y

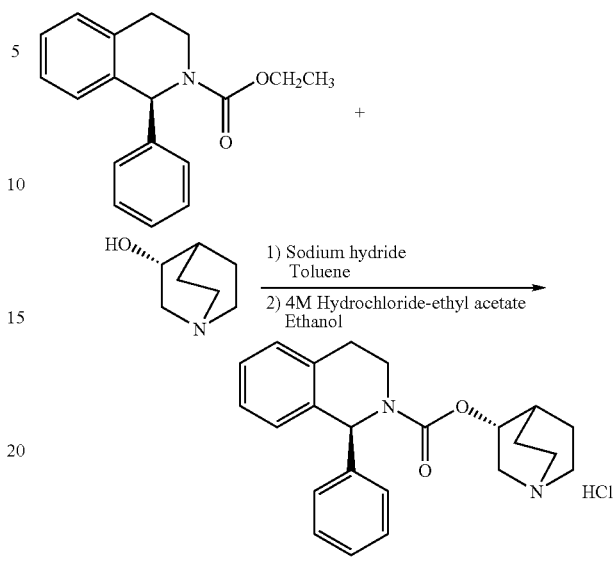

In addition, the following production method is known as a method for producing compounds having similar structures, but there is no case in which this production method was applied to the production of solifenacin (Patent Reference 4).

(c) Production Method Z

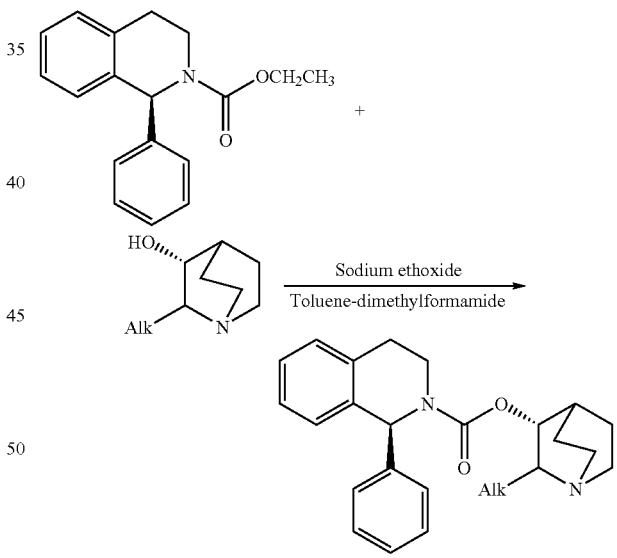

[In the formulae, Alk represents methyl or ethyl.]

Patent Reference 1: International Publication WO 96/20194
Patent Reference 2: International Publication WO 2003/6019
Patent Reference 3: JP-A-2002-104968
Patent Reference 4: JP-A-2003-267977
Non-patent Reference 1: *Current Opinion in Central & Peripheral Nervous System Investigational Drugs*, 2000, vol. 2, no. 3, pp. 321-325
Non-patent Reference 2: *Drugs of the Future*, 1999, vol. 24, no. 8, pp. 871-874

Non-patent Reference 3: *Naunyn-Schmiedeberg's Archives of Pharmacology*, 2002, vol. 366, no. 2, pp. 97-103

Non-patent Reference 4: *Japanese Journal of Pharmacology*, 2001, vol. 86, no. 3, pp. 281-288

DISCLOSURE OF THE INVENTION

Problems that the Invention is to Solve

However, as is described later, there were various problems regarding the production method X and production method Y of solifenacin or a salt thereof, so that concern has been directed toward the development of a method for producing solifenacin or a salt thereof, which is more efficient from the viewpoint of industrial production.

Means for Solving the Problems

The present inventors have conducted intensive studies on a new method for producing solifenacin or a salt thereof and found as a result that solifenacin or a salt thereof can be produced efficiently by the production method shown in the following, thereby resulting in the accomplishment of the invention.

That is, according to the invention, novel methods for producing solifenacin or a salt thereof shown in the following are provided.

1. A method for producing solifenacin or a salt thereof, which comprises allowing a compound represented by a formula (I)

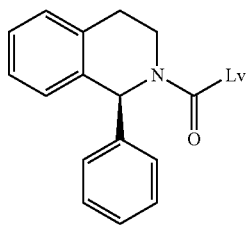

(I)

[in the formula, Lv represents 1H-imidazol-1-yl, 2,5-dioxopyrrolidin-1-yloxy, 3-methyl-1H-imidazol-3-ium-1-yl or chloro]

and (R)-quinuclidin-3-ol to undergo condensation.

As the Lv, 1H-imidazol-1-yl is desirable.

2. A method for producing solifenacin succinate, which comprises allowing succinic acid to react with a compound represented by a formula (II)

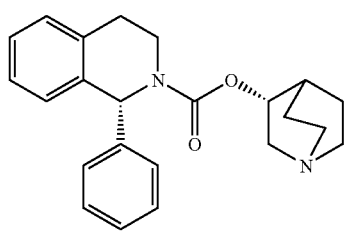

(II)

[in the formula, stereochemistry of the 1-position of phenyl-substituted tetrahydroisoquinoline is a mixture of (R)-form and (S)-form].

3. A method for producing solifenacin or a salt thereof, which comprises allowing a compound represented by a formula (III)

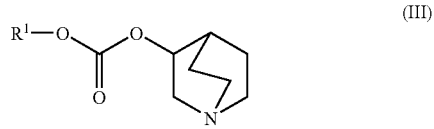

(III)

[in the formula, $R^1$ represents a lower alkyl which may be substituted]

and (S)-1-phenyl-1,2,3,4-tetrahydroisoquinoline or a salt thereof to undergo condensation.

As $R^2$, ethyl is preferable.

4. A method for producing solifenacin or a salt thereof, which comprises allowing a compound represented by a formula (IV)

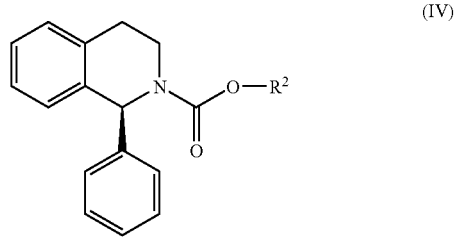

(IV)

[in the formula, $R^2$ represents a secondary lower alkyl or a tertiary lower alkyl, which may be respectively substituted] and (R)-quinuclidin-3-ol to undergo reaction in the presence of an alkali metal lower alkoxide.

As the $R^2$, isopropyl or tert-butyl is desirable.

In addition, as the lower alkoxide of the alkali metal lower alkoxide, a secondary lower alkoxide or a tertiary lower alkoxide is desirable, and a secondary lower alkoxide or tertiary lower alkoxide which corresponds to $R^2$ is particularly desirable.

EFFECT OF THE INVENTION (1) Production Method 1

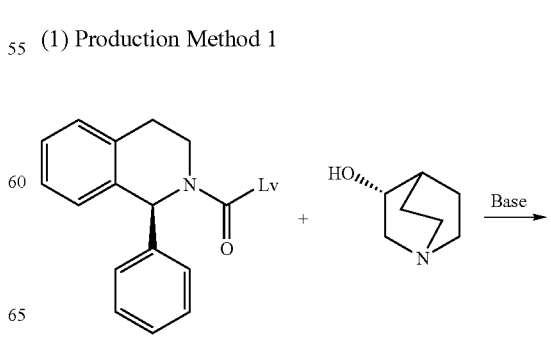

-continued

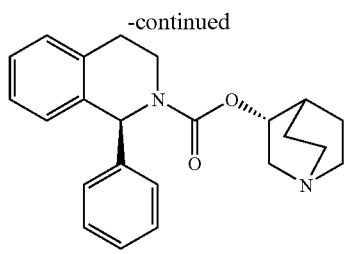

[In the formula, Lv represents 1H-imidazol-1-yl, 2,5-dioxopyrrolidin-1-yloxy, 3-methyl-1H-imidazol-3-ium-1-yl or chloro.]

This production method is a method for producing solifenacin, which uses (S)-2-(1H-imidazol-1-ylcarbonyl)-1-phenyl-1,2,3,4-tetrahydroisoquinoline, 1-({[(S)-1-phenyl-1,2,3,4-tetrahydroisoquinolin-2-yl]carbonyl}oxy)pyrrolidine-2,5-dione, (S)-2-(3-methyl-1H-imidazol-3-ium-1-ylcarbonyl)-1-phenyl-1,2,3,4-tetrahydroisoquinoline, or (S)-1-phenyl-1,2,3,4-tetrahydroisoquinolin-2-ylcarbonyl chloride, instead of the (S)-1-phenyl-1,2,3,4-tetrahydroisoquinoline-2-carboxylic acid ethyl ester used in the aforementioned production method Y as the starting material.

Since ethyl carboxylate is used as the starting material in the production method Y, ethanol (EtOH) is by-produced, and the by-produced EtOH launches a nucleophilic attack against the intended substance solifenacin in the presence of a base. Thus, it is necessary to carry out the reaction while removing EtOH from the reaction system, for example by the toluene azeotrope or the like, so that control of the reaction, particularly control of the evaporated amount of the solvent by distillation is essential, but such a control is very difficult to effect. However, According to this production method, imidazole, 1-hydroxypyrrolidine-2,5-dione, 3-methyl-1H-imidazol-3-ium or hydrochloric acid is by-produced, but these by-produced compounds do not launch a nucleophilic attack against the intended substance solifenacin in the presence of a base, and control of the reaction is not necessary.

In addition, when the production method Y was compared at a certain similar degree of scale with a method which uses (S)-2-(1H-imidazol-1-ylcarbonyl)-1-phenyl-1,2,3,4-tetrahydroisoquinoline, it was found that the production method Y requires approximately 8 hours of reaction time, and what is more, approximately from 5 to 15% of the starting material (S)-1-phenyl-1,2,3,4-tetrahydroisoquinoline-2-carboxylic acid ethyl ester remains, while the reaction time of this production method can be shortened by a factor of about 3 hours, and what is more, the starting material (S)-2-(1H-imidazol-1-ylcarbonyl)-1-phenyl-1,2,3,4-tetrahydroisoquinoline remains only about 0.3%. in addition, while solifenacin exists in four optical isomer forms due to the presence of 2 asymmetric centers, production of undesired optical isomers was about 7% by the production method Y, but production of undesired optical isomers was about 1% or less by the present production method.

Accordingly, this production method is a superior production method in comparison with the production method Y from the viewpoints that (i) control of the reaction is easy because it is not necessary to remove reaction byproducts from the reaction system, that (ii) the reaction time can be sharply shortened, that (iii) remaining of the starting material after completion of the reaction can be sharply reduced, and that (iv) formation of undesired optical isomers by the side reaction can be sharply reduced.

(2) Production Method (2)

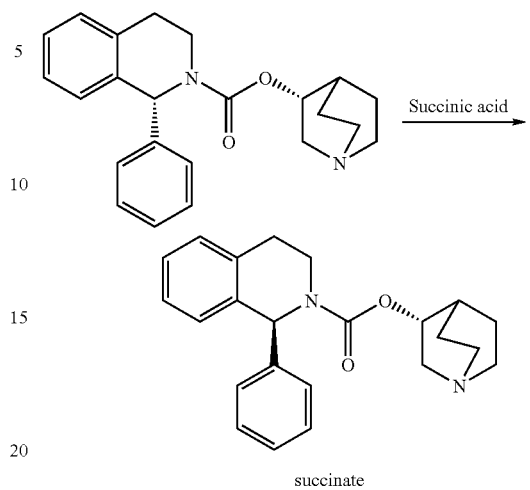

succinate

This method is a method for producing optically active solifenacin succinate by using a diastereomer mixture (1RS)-1-phenyl-1,2,3,4-tetrahydroisoquinoline-2-carboxylic acid (3R)-quinuclidin-3-yl ester as the material and carrying out optical resolution accompanied by the salt formation with succinic acid.

Conventionally, in carrying out production of solifenacin or a salt thereof, optically active solifenacin or a salt thereof was produced by producing solifenacin through the bonding of an optically active 1-phenyl-1,2,3,4-tetrahydroisoquinoline unit with a quinuclidin-3-ol unit, and applying a salt formation reaction to the optically active solifenacin as occasion demands.

However, in order to produce the optically active 1-phenyl-1,2,3,4-tetrahydroisoquinoline unit to be used as a starting material, it was essential to employ an operation such as optical resolution using tartaric acid, a reaction using an asymmetric catalyst, a resolution using chiral column or the like. In addition, such an operation which becomes necessary when produced as an optically active substance increases the number of steps in the industrial production process and also becomes a cause of making the operation more complex.

On the other hand, according to this production method, a tetrahydroquinoline 1-position diastereomer mixture can be used as the 1-phenyl-1,2,3,4-tetrahydroisoquinoline-2-carboxylic acid quinuclidin-3-yl ester before carrying out a salt formation reaction, so that it is able to omit steps which are necessary in producing the optically active 1-phenyl-1,2,3,4-tetrahydroisoquinoline unit, such as salt formation using an acid having asymmetric center, optical resolution and subsequent desalting; asymmetric synthesis using an expensive asymmetric catalyst; and/or separation by a chiral column; and the like. That is, according to the invention, the number of steps can be shortened in the industrial production process so that solifenacin succinate can be produced more efficiently.

In addition, it is very surprising that a desired optical isomer alone can be separated merely by an operation to make a salt of a diastereomer mixture using succinic acid or the like acid or base having no asymmetric center.

Thus, this production method is (i) an efficient and excellent production method from the viewpoint that the operations generally necessary in producing the solifenacin starting material, 1-phenyl-1,2,3,4-tetrahydroisoquinoline unit, as an optically active substance are not required because it is not necessary to produce it as an optically active substance, and is (ii) a quite surprising production method from the viewpoint that solifenacin succinate as a desired optical isomer can be separated by making a diastereomer mixture, (1RS)-1-phenyl-1,2,3,4-tetrahydroisoquinoline-2-carboxylic acid (3R)-quinuclidin-3-yl ester, into a salt using succinic acid which does not have asymmetric center.

(3) Production Method 3

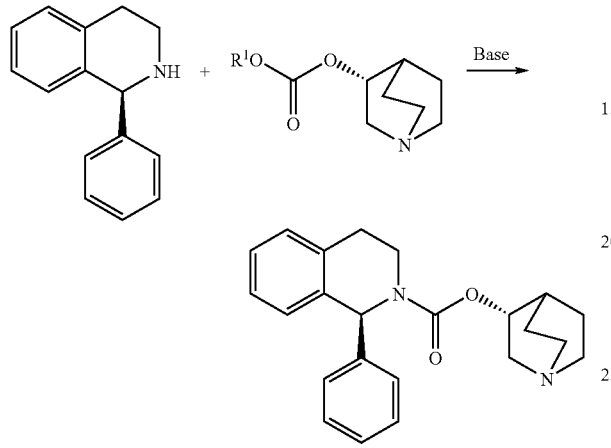

[In the formula, $R^1$ represents a lower alkyl which maybe substituted.]

This production method is a method for producing solifenacin, which uses an lower alkyl (R)-quinuclidin-3-yl carbonate instead of the (R)-quinuclidin-3-yl chloroformate used in the aforementioned production method X as the starting material.

In the production method X, chloroformate is used as the starting material, and this chloroformate is produced from (R)-quinuclidin-3-ol and phosgene or a phosgene derivative. As the phosgene derivative, diphosgene and triphosgene can be exemplified. However, since it is known that phosgene causes a respiratory organ disorder when inhaled, it is difficult to use it in the industrial production. Even when diphosgene, triphosgene or the like phosgene derivative is used, it easily forms phosgene when decomposed, so that it cannot be said that this is suited for the industrial production. Also, this type of reaction requires control of the reaction in an atmosphere of argon, nitrogen or the like inert gas under a non-aqueous condition, so that the operation becomes complex. In addition, since quinuclidinyl chloroformate is apt to be decomposed, it becomes necessary to prepare it when used.

On the other hand, according to the present production method, a lower alkyl quinuclidinyl carbonate is used as the active species, which can be produced from quinuclidinol and a lower alkyl chlorocarbonate safely in view of industrial production and also easily with high yield, and it is not necessary to prepare the lower alkyl quinuclidinyl carbonate at the time of its use, because the compound is stable at from low temperature to ordinary temperature.

Accordingly, this production method is a superior production method in comparison with the production method X from the viewpoints that (i) since phosgene or a phosgene derivative having extremely high toxicity is not used, this is excellent in safety in view of industrial production, that (ii) since a inert gas atmosphere and a non-aqueous condition are not required for the production of a lower alkyl carbonate quinuclidine ester as the active species, the production steps do not become complex, and that (iii) since the lower alkyl quinuclidinyl carbonate as the active species is stable at from low temperature to ordinary temperature, its storage is possible and its preparation when used is not necessary.

(4) Production Method 4

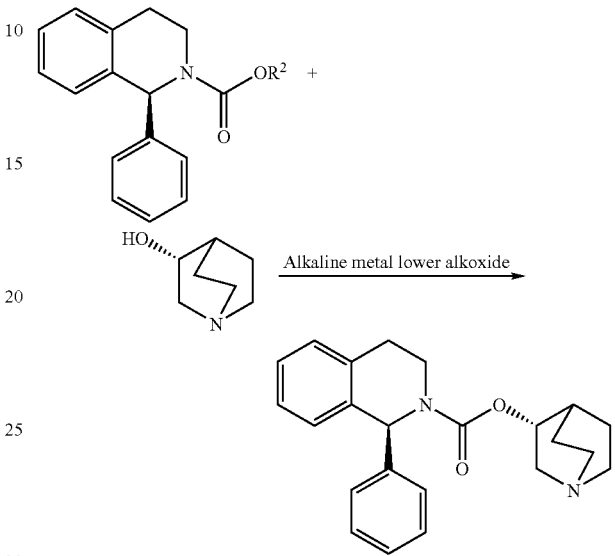

[In the formula, $R^2$ represents a secondary lower alkyl or a tertiary lower alkyl, which may be respectively substituted.]

This production method is a method for producing solifenacin, which uses an alkali metal lower alkoxide instead of the sodium hydride used as a base in the aforementioned production method Y, and also uses an (S)-1-phenyl-1,2,3,4-tetrahydroisoquinoline-2-carboxylic acid secondary lower alkyl or tertiary lower alkyl ester, wherein said alkyl may be respectively substituted, instead of the (1S)-1-phenyl-1,2,3,4-tetrahydroisoquinoline-2-carboxylic acid ethyl ester used as the starting material in the aforementioned production method Y.

Sodium hydride is used in the production method Y, which has a danger of causing firing and a problem of causing contamination with the containing mineral oil. However, this production method is characterized by the use of an alkali metal lower alkoxide which does not have such problems.

In addition, as shown in the following Reference Example 2, Reference Example 3 and Reference Example 4, it was confirmed that when solifenacin is produced using ethyl ester, methyl ester, benzyl ester or the like substitutable primary lower alkyl ester of (S)-1-phenyl-1,2,3,4-tetrahydroisoquinoline-2-carboxylic acid as the starting material, a compound in which a primary lower alkyl which may be substituted is added to the solifenacin 2'-position, namely the quinuclidine 2-position, is by-produced as an impurity. On the other hand, by-production of a compound in which a primary lower alkyl which may be substituted is added to the solifenacin 2'-position, namely the quinuclidine 2-position, found in Reference Example 2, Reference Example 3 and Reference Example 4, was not found by this production method, due to the use of a respectively substitutable secondary lower alkyl or tertiary lower alkyl, namely $R^2$, ester of (S)-1-phenyl-1,2,3,4-tetrahydroisoquinoline-2-carboxylic acid as the starting material. Especially, when a secondary lower alkoxide, a tertiary lower alkoxide or a lower alkoxide which corresponds to $R^2$ was used as the lower alkoxide of the alkali metal lower alkoxide, by-production of the compound in which a lower alkyl was added to the aforementioned quinuclidine 2-position was not found.

Accordingly, this production method is (i) a superior method in comparison with the production method Y from the viewpoint that an alkali metal lower alkoxide having reduced danger in the industrial production can be used, and is (ii) a quite surprising production method from the viewpoint that, in comparison with the production method in which ethyl ester, methyl ester, benzyl ester or the like substitutable primary lower alkyl ester of (S)-1-phenyl-1,2,3,4-tetrahydroisoquinoline-2-carboxylic acid is used as the starting material, a compound in which a lower alkyl is added to the quinuclidine 2-position is not by-produced in the solifenacin-containing composition produced by this production method which uses a respectively substitutable secondary lower alkyl or tertiary lower alkyl ester of (S)-1-phenyl-1,2,3,4-tetrahydroisoquinoline-2-carboxylic acid as the starting material.

BRIEF DESCRIPTION OF THE INVENTION

FIG. 1 is a chart in which the composition concerning compound A, compound B and compound C of the solifenacin obtained in Reference Example 1 was measured by HPLC. The peak of about 33.3 minutes in retention time shows solifenacin, and the peaks of about 15.6 minutes, about 19.8 minutes and about 16.9 minutes in retention time respectively show the compound A, compound B and compound C.

Figure 2:
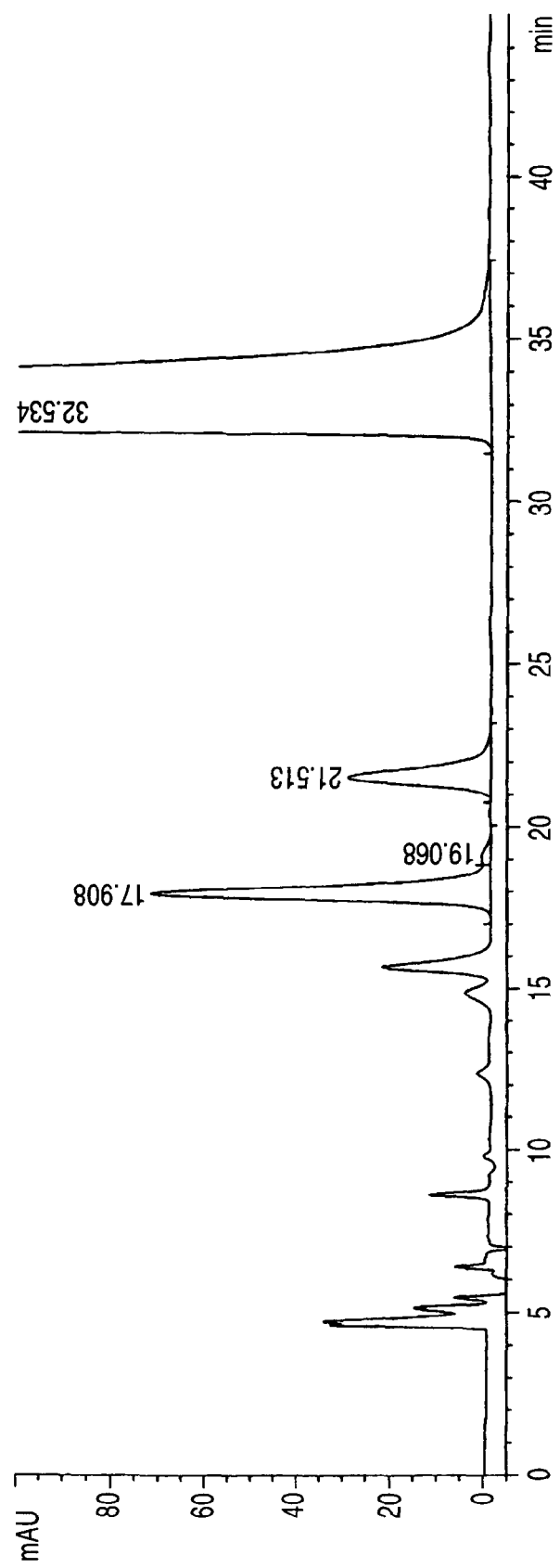

FIG. 2 is a chart in which the composition concerning compound A, compound B and compound C of the solifenacin-containing EtOAc solution obtained in Reference Example 2 was measured by HPLC. The peak of about 32.5 minutes in retention time shows solifenacin, and the peaks of about 17.9 minutes, about 21.5 minutes and about 19.1 minutes in retention time respectively show the compound A, compound B and compound C.

Figure 3:
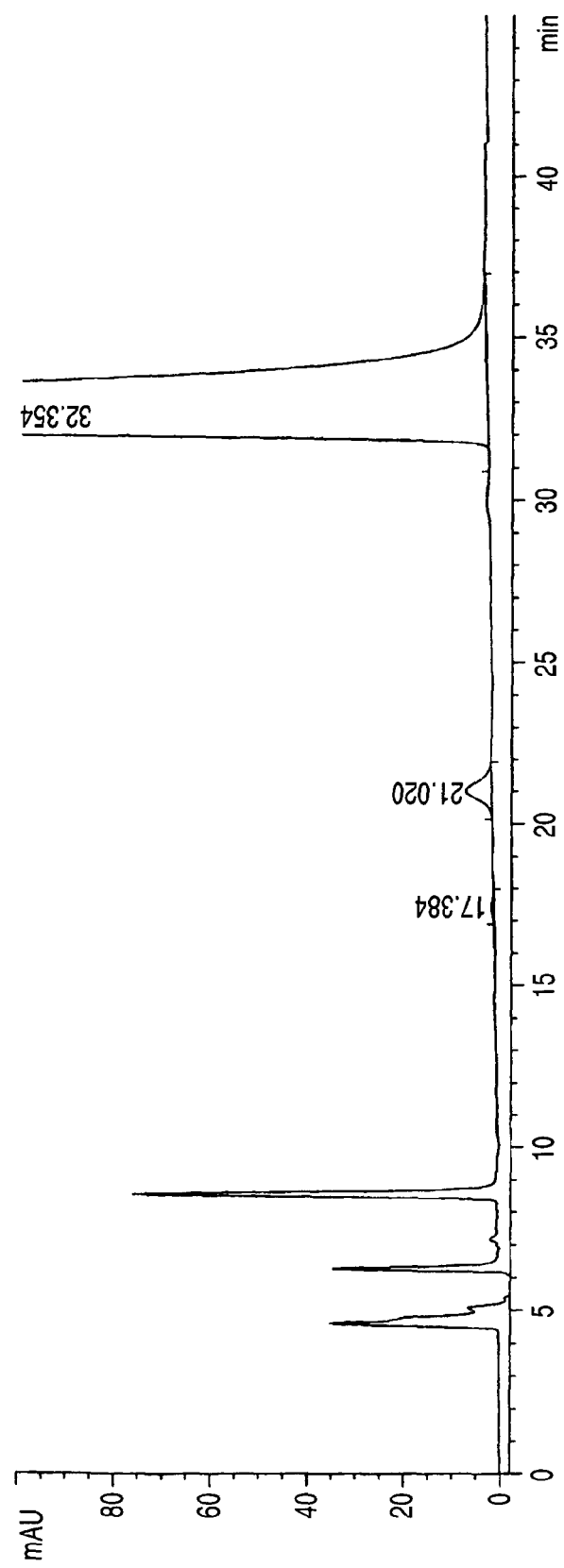

FIG. 3 is a chart in which the composition concerning compound A, compound B and compound C of the solifenacin before salt formation with succinic acid, obtained in Example 1A, was measured by HPLC. The peak of about 32.4 minutes in retention time shows solifenacin, and the peaks of about 17.4 minutes and about 21.0 minutes in retention time respectively show the compound A and compound B.

Figure 4:
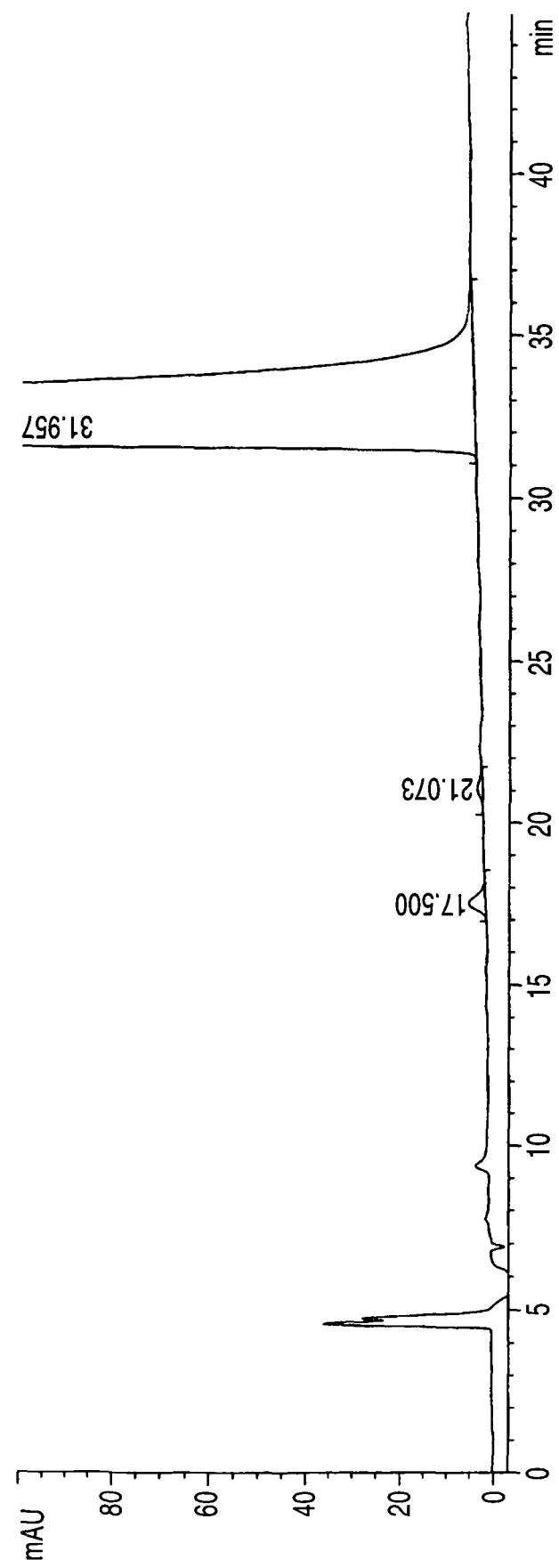

FIG. 4 is a chart in which the composition concerning compound A and compound B of the solifenacin succinate obtained in Example 2 was measured by HPLC. The peak of about 32.0 minutes in retention time shows solifenacin, and the peaks of about 17.5 minutes and about 21.1 minutes in retention time respectively show the compound A and compound B.

BEST MODE FOR CARRYING OUT THE INVENTION

The following further describes the invention.

The term "lower alkyl" as used herein means a straight chain or branched chain $C_{1-6}$ alkyl, and its illustrative examples include methyl, ethyl, propyl, butyl, pentyl, hexyl, isopropyl, tert-butyl and the like.

Accordingly, methyl, ethyl, n-propyl, n-butyl, 2-methylpropan-1-yl and the like can be cited as illustrative examples of the "primary lower alkyl", and isopropyl, butan-2-yl, pentan-3-yl, tert-butyl, 2-methylbutan-2-yl, 3-methylpentan-3-yl and the like can be cited as illustrative examples of the "secondary lower alkyl or tertiary lower alkyl".

In addition, the "lower alkoxide" is an —O-lower alkyl which corresponds to the aforementioned lower alkyl. Accordingly, methoxy, ethoxy, n-propoxy, n-butoxy, 2-methylpropan-1-yloxy and the like can be cited as illustrative examples of the "primary lower alkoxide," and 2-propoxy, butan-2-yloxy, pentan-3-yloxy, tert-butoxy, 2-methylbutan-2-yloxy, 3-methylpentan-3-yloxy and the like can be cited as illustrative examples of the "secondary lower alkoxide or tertiary lower alkoxide".

The acceptable substituent group of $R^1$ and $R^2$ may be any group which is generally acceptable to be substituted to lower alkyl, and phenyl and the like can be illustratively cited. In this connection, in the "primary lower alkyl", its carbon atom having linking arm is substituted by at least 2 hydrogen atoms.

The "alkali metal lower alkoxide" is a salt of an alcohol which corresponds to the aforementioned lower alkyl with an alkali metal, and lithium, sodium, potassium and the like can be exemplified as the alkali metal, of which sodium or potassium is preferred. As the "alkali metal lower alkoxide", sodium methoxide, sodium ethoxide, sodium propoxide, sodium isopropoxide, sodium butoxide, sodium tert-butoxide, sodium benzyloxide, potassium methoxide, potassium ethoxide, potassium tert-butoxide and the like can be illustratively exemplified. In this connection, regarding the alkali metal lower alkoxide to be used in the production, it is desirable to use an alkali metal lower alkoxide which corresponds to the —O-lower alkyl group existing in the molecule of the starting material.

The "base" may be any base which is sufficient enough for the hydroxyl group of quinuclidinol or the amino group of tetrahydroisoquinolin to carry out nucleophilic attack, and its illustrative examples include an alkali metal lower alkoxide; sodium hydroxide, potassium hydroxide or the like hydroxide; sodium hydride, potassium hydride, lithium hydride or the like hydride; triethylamine, diisopropylethylamine or the like tertiary amine; lithium diisopropylamide, potassium hexamethyldisilazide, sodium hexamethyldisilazide, butyl lithium or the like alkali metal reagent; or the like, and the production can also be carried out by adding 4-(N,N-dimethylamino)pyridine or the like catalyst.

The "salt thereof" of the "solifenacin or a salt thereof" may be any salt of solifenacin with a pharmacologically acceptable acid, and illustratively, an acid addition salt with hydrochloric acid, sulfuric acid or the like inorganic salt; or with succinic acid, acetic acid, oxalic acid, malonic acid or the like organic acid; can be exemplified. Preferred as the "solifenacin or a salt thereof" is solifenacin or solifenacin succinate.

Also, the term percentage content as used herein represents the ratio of area of each substance measured by an HPLC analysis when solifenacin or a salt thereof is defined as 100%, and is a percentage content measured by the HPLC analysis under the conditions shown in Examples which are described later or under conditions proportional thereto. In this connection, each of the substances is detected as a basic substance resulting from the removal of the addition salt.

In addition, the invention also includes a production method and a composition, which uses a compound, so-called labeled compound, in which the atoms that constitute solifenacin, a starting material thereof and/or the solifenacin derivative represented by the aforementioned (I) are partially or entirely replaced by a radioisotope.

The production method 1 is a method for producing solifenacin, in which (S)-2-(1H-imidazol-1-ylcarbonyl)-1-phenyl-1,2,3,4-tetrahydroisoquinoline, 1-({[(S)-1-phenyl-1,2,3,4-tetrahydroisoquinolin-2-yl]carbonyl}oxy)pyrrolidine-2,5-dione, (S)-2-(3-methyl-1H-imidazol-3-ium-1-ylcarbonyl)-1- phenyl-1,2,3,4-tetrahydroisoquinoline or (S)-1-phenyl-1,2,3,4-tetrahydroisoquinolin-2-ylcarbonyl chloride is allowed to react with (R)-quinuclidin-3-ol in the presence of a base.

The reaction can be carried out in a reaction inert solvent, such as benzene, toluene, xylene, mesitylene and the like aromatic hydrocarbons; diethyl ether, diisopropyl ether, tetrahydrofuran, dioxane, dimethoxyethane and the like ethers; dichloromethane, 1,2-dichloroethane, chloroform and the like halogenated hydrocarbons; N,N-dimethylformamide (DMF), N,N-dimethylacetamide, N-methylpyrrolidone, dimethyl sulfoxide and the like aprotic polar solvents; and the like or a mixture thereof, using equimolar of said starting materials or one of them in an excess amount, and at from cooling to room temperature, from room temperature to heating or from heating to under reflux, and it is desirable to carry it out from under heating to under reflux. The base can be used in an equivalent to excess amount, and it is desirable to carry out the reaction using a hydride, preferably sodium hydride.

In this connection, the Lv in the aforementioned formula, which represents 1H-imidazol-1-yl, 2,5-dioxopyrrolidin-1-yloxy, 3-methyl-1H-imidazol-3-ium-1-yl or chloro, is preferably 1H-imidazol-1-yl, 2,5-dioxopyrrolidin-1-yloxy or 3-methyl-1H-imidazol-3-ium-1-yl, most preferably 1H-imidazol-1-yl.

In addition, (S)-2-(1H-imidazol-1-ylcarbonyl)-1-phenyl-1,2,3,4-tetrahydroisoquinoline, 1-({[(S)-1-phenyl-1,2,3,4-tetrahydroisoquinolin-2-yl]carbonyl}oxy)pyrrolidine-2,5-dione, (S)-2-(3-methyl-1H-imidazol-3-ium-1-ylcarbonyl)-1-phenyl-1,2,3,4-tetrahydroisoquinoline or (S)-1-phenyl-1,2,3,4-tetrahydroisoquinolin-2-ylcarbonyl chloride can be produced by carrying out condensation of (S)-1-phenyl-1,2,3,4-tetrahydroisoquinoline with 1,1'-carbonyldiimidazole, N,N'-disuccinimidyl carbonate, phosgene or a phosgene derivative or with 1-methylimidazole, phosgene or a phosgene derivative in accordance with a usual method.

The production method 2 is a method for producing solifenacin succinate in which succinic acid is allowed to react with (1RS)-1-phenyl-1,2,3,4-tetrahydroisoquinoline-2-carboxylic acid (3R)-quinuclidin-3-yl ester.

The solvent to be used in the reaction may be any solvent which is generally used in a reaction in which a basic substance such as solifenacin is converted into its acid addition salt, and an organic solvent, water or a mixture thereof can be exemplified. More illustrative examples include methanol, EtOH, 1-propanol, 2-propanol, 1-butanol, 2-butanol, tert-butanol and the like alcohols; ethyl acetate (EtOAc), n-propyl acetate, n-butyl acetate, methyl propionate, ethyl propionate and the like esters; ethers; acetone, methyl ethyl ketone and the like ketones; aprotic polar solvents; acetonitrile; halogenated hydrocarbons; aromatic hydrocarbons; hexane, heptane and the like saturated hydrocarbons; water and the like, or a mixed solvent of optional species of solvents selected from them. Preferred are mixed solvents of alcohols and esters, and particularly preferred among them is a mixed solvent of EtOH and EtOAc.

Succinic acid can be used in an equivalent amount of an excess amount. In addition, succinic acid can also be dissolved by adding it and then heating it when dissolved. Solifenacin succinate as the desired one of the stereoisomers can be obtained when the thus obtained solution is cooled, and the resulting precipitate is collected by filtration in the usual way, washed using an appropriate solvent and then dried. In this case, though it depends on the scale of the process, it is desirable that the cooling rate is not rapid.

Also, regarding the solvent to be used in the washing, any solvent which has small solubility for solifenacin succinate can be used, and preferred are ethers, esters and alcohols or a mixed solvent of two or more solvents selected from the group consisting of these solvents. The drying can be carried out by heating, under a reduced pressure or by heating under a reduced pressure.

In addition, the (1RS)-1-phenyl-1,2,3,4-tetrahydroisoquinoline-2-carboxylic acid (3R)-quinuclidin-3-yl ester can be produced, for example, by employing the method described in the Patent Reference 1, and the following production methods can be exemplified illustratively.

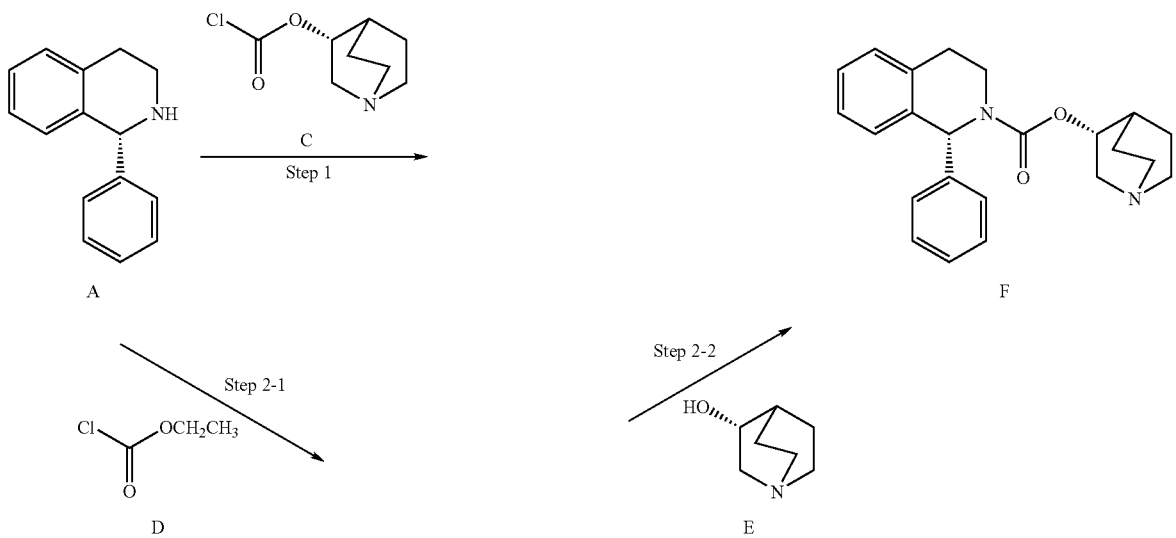

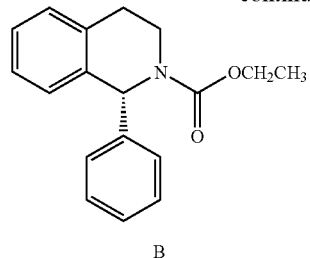

B

By one of them, the racemic compound (I) can be produced by allowing the (R)-quinuclidin-3-yl chloroformate represented by C or a salt thereof, which is derived by 1 step from commercially available (R)-quinuclidin-3-ol, to react with the racemic tetrahydroisoquinolin represented by A or a salt thereof in the presence of a base or in a basic solvent. Illustratively, the method described in Example 7 of the aforementioned Patent Reference 1 can for example by employed.

As another embodiment, the production method by step 2-1 and step 2-2 can be cited. The racemic compound (I) can be produced by allowing commercially available (R)-quinuclidin-3-ol to react, in the presence of a base or in a basic solvent, with a carbamate represented by B which is obtained by allowing ethyl chloroformate represented by D to react with the racemic tetrahydroisoquinolin represented by A or a salt thereof in the presence of a base or in a basic solvent. Illustratively, the method of Reference Example 1 or Example 8 of the aforementioned Patent Reference 1 can for example be employed.

In addition, (1RS)-1-phenyl-1,2,3,4-tetrahydroisoquinoline-2-carboxylic acid (3R)-quinuclidin-3-yl ester can also be produced by employing the solifenacin production method 1, production method 3 or production method 4 of the invention.

The production method 3 is a method for producing solifenacin in which (S)-1-phenyl-1,2,3,4-tetrahydroisoquinoline is allowed to react with an lower alkyl (R)-quinuclidin-3-yl carbonate.

The reaction can be carried out in a reaction inert solvent, such as of aromatic hydrocarbons; ethers; halogenated hydrocarbons; aprotic polar solvents; and the like, or a mixture thereof, using said starting materials at equimolar level or one of them in an excess amount, preferably equimolar level. In addition, the reaction can be carried out at a temperature of from cooling to room temperature, from room temperature to heating, or from heating to under reflux, and it is desirable to carry out the reaction under reflux while evaporating the solvent. The base can be used in an amount of from a catalytically effective amount to an excess amount, preferably from 0.1 to 2.0 equivalents, more preferably from 0.1 to 1.0 equivalent, further preferably from 0.2 to 0.6 equivalent. It is desirable to carry out the reaction using an alkali metal lower alkoxide, preferably an alkali metal lower alkoxide which corresponds to $R^1$.

The production method 4 is a method for producing solifenacin in which (S)-1-phenyl-1,2,3,4-tetrahydroisoquinoline-2-carboxylic acid secondary lower alkyl or tertiary lower alkyl ester is allowed to react with (R)-quinuclidin-3-ol in the presence of an alkali metal lower alkoxide.

The reaction can be carried out in a reaction inert solvent, such as of aromatic hydrocarbons; ethers; halogenated hydrocarbons; aprotic polar solvents; and the like, or a mixture thereof, using said starting materials at equimolar level or one of them in an excess amount, at a temperature of from cooling to room temperature, from room temperature to heating, or from heating to under reflux, and it is desirable to carry out the reaction under reflux while evaporating the solvent. The alkali metal lower alkoxide can be used in an amount of from a catalytically effective amount to an excess amount, but it is desirable to use preferably from 0.1 to 1.2 equivalents, more preferably from 0.15 to 0.4 equivalent, of an alkali metal lower alkoxide, and it is desirable to carry out the reaction using an alkali metal lower alkoxide which corresponds to $R^2$.

EXAMPLES

The following illustratively describes the invention based on Examples, but the invention is not restricted by these Examples.

Reference Example 1

A mixture of 8 liters of water and 3.17 kg of potassium carbonate was added to a mixture of 4.00 kg of (S)-1-phenyl-1,2,3,4-tetrahydroisoquinoline and 40 liters of toluene, and 2.49 kg of ethyl chloroformate was added dropwise thereto and stirred for 2 hours. A 20 liter portion of water was added to this reaction solution, the water layer was separated, and the organic layer was washed with 20 liters of water. After evaporation of the solvent under a reduced pressure, 43.7 liters of toluene and 4.9 liters of DMF were added thereto, and 2.64 kg of (R)-quinuclidin-3-ol and 0.188 kg of sodium hydride were added thereto at room temperature and heated for 8 hours while evaporating the solvent. A 49 liter portion of toluene and 25 liters of water were added to this reaction mixture which was subsequently cooled to room temperature, and then the water layer was separated and the organic layer was washed with 25 liters of water. This organic layer was then extracted with 49 liters of 4% hydrochloric acid, the thus obtained water layer was mixed with 5.8 kg of potassium carbonate and extracted with EtOAc, and the organic layer was concentrated under a reduced pressure to obtain 5.32 kg of (1S)-1-phenyl-1,2,3,4-tetrahydroisoquinoline-2-carboxylic acid (3R)-quinuclidin-3-yl ester (to be referred to as "solifenacin" hereinafter).

The optical isomer content of the solifenacin obtained in Reference Example 1 is shown in Table 1 as the percentage content when solifenacin is defined as 100%. Also, measured data of the determination of the composition concerning compound A, compound B and compound C as optical isomers of the solifenacin obtained in Reference Example 1 is shown in FIG. 1.

In this connection, the compound A, compound B and compound C have the following structures.

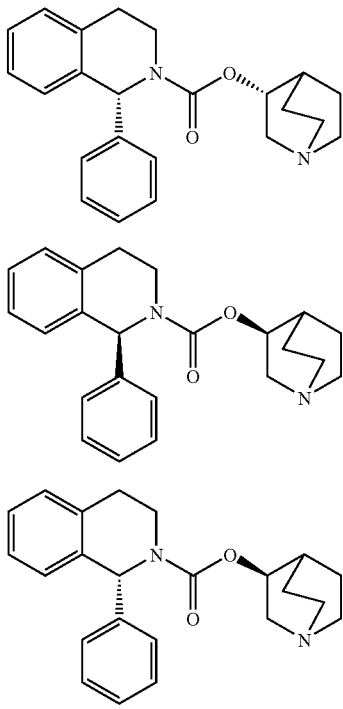

Compound A

Compound B

Compound C

In this connection, determination of the compound A, compound B and compound C was carried out by the following method.

A 0.25 g portion of the obtained composition was dissolved in a mixed liquid of hexane/2-propanol (1:1), and the total volume was adjusted to 100 ml to be used as a sample solution. The mixed liquid of hexane/2-propanol (1:1) was added to 1 ml of this sample solution, and the total volume was adjusted to 100 ml to be used as a standard solution. A 10 μl portion of each of the sample solution and standard solution was tested by a liquid chromatography under the following conditions, respective peak areas of the respective solutions were measured by an automatic integration method, and the amount of impurities was calculated by the following equation.

Percentage content of respective impurities (%)=$ATi/AS$

[In the formula, ATi represents peak areas of respective impurities of the sample solution, and AS represents peak area of solifenacin of the standard solution.]

<Test Conditions>
Detector: ultraviolet absorptiometer (measuring wavelength: 220 nm)
Column: CHIRALPAK AD-H (250 mm×4.6 mm ID, mfd. by Daicel Chemical)
Column temperature: 20° C.
Mobile phase: hexane/2-propanol/diethylamine mixed liquid (800:200:1)
Flow rate: adjusted such that retention time of solifenacin becomes about. 35 minutes (about 1 ml/min)

Reference Example 2

A mixture of 360 liters of water and 83.2 kg of potassium carbonate was added to a mixture of 120 kg of (S)-1-phenyl-1,2,3,4-tetrahydroisoquinoline and 600 liters of toluene, and after cooling to 10° C., 65.3 kg of ethyl chloroformate was added dropwise thereto and stirred at 25° C. for 2 hours. The water layer was separated and the organic layer was washed with 360 liters of water. After evaporation of 290 liters of the solvent under a reduced pressure, 1320 liters of toluene and 81 liters of DMF were added thereto, and 87.5 kg of (R)-quinuclidin-3-ol and 7.8 kg of sodium ethoxide were added thereto at room temperature and heated for 8 hours while evaporating the solvent. A 480 liter portion of toluene and 400 liters of water were added to this reaction solution which was subsequently cooled to room temperature, and then the water layer was separated and the organic layer was washed with 400 liters of water. This organic layer was then extracted with 77.4 kg of concentrated hydrochloric acid and 440 liters of water, the thus obtained water layer was mixed with a mixture of 126.8 kg of potassium carbonate and 320 liters of water and extracted with 810 liters of EtOAc. This organic layer was washed with 160 liters of water and then mixed with 160 liters of EtOH and 240 liters of EtOAc. A 820 liter portion of the solvent of this solution was evaporated by atmospheric distillation to obtain 527.8 kg of an EtOAc solution containing solifenacin.

The optical isomer content of solifenacin of the solifenacin-containing EtOAc solution obtained in Reference Example 2 is shown in Table 1 as the percentage content when solifenacin is defined as 100%. Also, measured data of the determination of the composition concerning compound A, compound B and compound C as optical isomers of solifenacin of the solifenacin-containing EtOAc solution obtained in Reference Example 2 is shown in FIG. 2.

The content of compound D of the solifenacin obtained in Reference Example 2 is shown in Table 2 as the percentage content when solifenacin is defined as 100%.

In this connection, the compound D has the following structure.

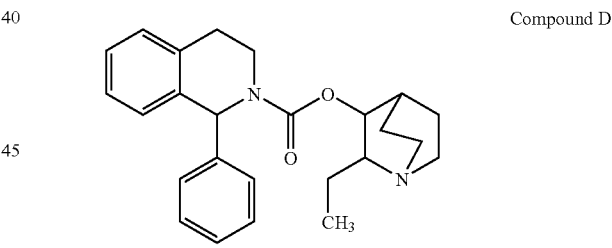

Compound D

In this connection, determination of the compound D was carried out by the following method.

A 0.05 g portion of the composition obtained in the aforementioned Reference Example 2 was dissolved in a liquid prepared by adding 300 ml of acetonitrile to 700 ml of a liquid which had been prepared by dissolving 8.7 g of dipotassium hydrogenphosphate in 1000 ml of water and adjusted to pH 6.0 by adding phosphoric acid (to be referred to as liquid P hereinafter), and the total volume was adjusted to 100 ml to be used as a sample solution. The liquid P was added to 1 ml of this sample solution, and the total volume was adjusted to 100 ml to be used as a standard solution. A 10 μl portion of each of the sample solution and standard solution was tested by a liquid chromatography under the following conditions, respective peak areas of the respective solutions were measured by an automatic integration method, and the amount of impurities was calculated by the following equation.

Percentage content of respective impurities
(%)=ADTi/ADS

[In the formula, ADTi represents peak areas of respective impurities of the sample solution, and ADS represents peak area of solifenacin of the standard solution.]

<Test Conditions>
Detector: ultraviolet absorptiometer (measuring wavelength: 210 nm)
Column: Develosil ODS-UG-5 (150 mm×4.6 mm ID, mfd. by Nomura Chemical) or an equivalent column
Column temperature: 40° C.
Mobile phase: a liquid prepared by adding 200 ml of acetonitrile, 100 ml of 2-propanol and 50 ml of methanol to 650 ml of a liquid which had been prepared by dissolving 8.7 g of dipotassium hydrogenphosphate in 1000 ml of water and adjusted to pH 6.0 by adding phosphoric acid
Flow rate: about 1 ml/min Reference Example 3

A solifenacin solution containing 1-phenyl-1,2,3,4-tetrahydroisoquinoline-2-carboxylic acid 2-methylquinuclidin-3-yl ester (to be referred to as "compound E" hereinafter) was obtained by allowing 9.00 g of (S)-1-phenyl-1,2,3,4-tetrahydroisoquinoline-2-carboxylic acid methyl ester to react with 5.14 g of (R)-quinuclidin-3-ol for 8 hours in a mixture of 90 ml of toluene and 4.5 ml of DMF in the presence of 0.36 g of sodium methoxide, while evaporating the solvents.

The content of compound E of the solifenacin obtained in Reference Example 3 is shown in Table 2 as the percentage content when solifenacin is defined as 100%.

In this connection, determination of the compound E was carried out by the following method.

A 0.01 g portion of the composition obtained in the aforementioned Reference Example 3 was dissolved in the liquid P, and the total volume was adjusted to 10 ml to be used as a sample solution. A 10 µl portion of this sample solution was tested by a liquid chromatography under the following conditions, and the peak area was measured by an automatic integration method.

<Test Conditions>
Detector: ultraviolet absorptiometer (measuring wavelength: 210 nm)
Column: Develosil ODS-UG-5 (150 mm×4.6 mm ID, mfd. by Nomura Chemical)
Column temperature: 40° C.
Mobile phase: liquid P
Flow rate: about 1 ml/min Reference Example 4

A 25.0 g portion of (S)-1-phenyl-1,2,3,4-tetrahydroisoquinoline and 24.5 g of benzyl chloride carbonate were added to a mixture of 125 ml of toluene, 19.8 g of potassium carbonate and 75 ml of water and stirred at 20° C. for 4 hours, and the organic layer was washed with 75 ml of water. The thus obtained organic layer was concentrated under a reduced pressure, purified by a silica gel column chromatography and then dried to obtain 38.0 g of (S)-1-phenyl-1,2,3,4-tetrahydroisoquinoline-2-carboxylic acid benzyl ester ($^1$H-NMR (DMSO-$d_6$, tetramethylsilane internal standard): δ 2.73-2.83 (1H, m), 2.84-2.94 (1H, m), 3.31-3.41 (1H, m), 3.86-3.96 (1H, m), 5.12 (1H, d, J=12.8 Hz), 5.18 (1H, d, J=12.8 Hz), 6.28 (1H, s), 7.10-7.38 (14H, m), mass spectrum: m/z=344 [M+H]$^+$ (FAB)).

In a mixture of sodium benzyl alkoxide prepared from 0.19 g of benzyl alcohol and 0.04 g of metallic sodium with 15 ml of toluene and 0.75 ml of DMF, 1.33 g of (R)-quinuclidin-3-ol was allowed to react with 3.00 g of (S)-1-phenyl-1,2,3,4-tetrahydroisoquinoline-2-carboxylic acid benzyl ester for 8 hours while evaporating the solvents, thereby obtaining 1.38 g of 1-phenyl-1,2,3,4-tetrahydroisoquinoline-2-carboxylic acid 2-benzylquinuclidin-3-yl ester (to be referred to as "compound F" hereinafter).

The content of compound F of the solifenacin obtained in Reference Example 4 is shown in Table 2 as the percentage content when solifenacin is defined as 100%.

In this connection, determination of the compound F was carried out by the following method.

A 0.03 g portion of the composition obtained in the aforementioned Reference Example 4 was mixed with the liquid P, and the total volume was adjusted to 10 ml to be used as a sample solution. The liquid P was added to 1 ml of this sample solution, and the total volume was adjusted to 200 ml to be used as a standard solution. A 20 µl portion of the sample solution and standard solution was tested by a liquid chromatography under the following conditions, respective peak areas of the respective solutions were measured by an automatic integration method, and the amount of impurities was calculated by the following equation.

Percentage content of respective impurities (%)=ATi/AS/2

[In the formula, ATi represents peak areas of respective impurities of the sample solution, and AS represents peak area of solifenacin of the standard solution.]

<Test Conditions>
Detector: ultraviolet absorptiometer (measuring wavelength: 210 nm)
Column: ODS-A,A-302 (150 mm×4.6 mm ID, mfd. by YMC)
Column temperature: 40° C.
Mobile phase: liquid P
Flow rate: about 1 ml/min Example 1A A 4.26 g portion of 1,1'-carbonyldiimidazole was added to 5.00 g of (S)-1-phenyl-1,2,3,4-tetrahydroisoquinoline and 25 ml of toluene and stirred at room temperature for 30 minutes. By adding 25 ml of water thereto, the water layer was separated, the organic layer was washed with 25 ml of water, and the solvent was evaporated under a reduced pressure. A 10 ml portion of toluene was added to the residue. This solution was added dropwise at room temperature to a solution prepared by adding 1.00 g of sodium hydride to a mixture of 3.65 g of (R)-quinuclidin-3-ol, 25 ml of toluene and 5 ml of DMF and heating to 100° C., and 5 ml of toluene was further added thereto. This was heated at 110° C. for 3 hours, cooled and mixed with 25 ml of water, and the water layer was separated. This was again washed with 25 ml of water, and the organic layer was extracted with a mixture of 3.25 g of concentrated hydrochloric acid and 18 ml of water. 34 ml of EtOAc, and a mixture of 5.28 g of potassium carbonate and 14 ml of water were added to the thus obtained water layer, the thus obtained organic layer was washed with 7 ml of water, and then the solvent was evaporated under a reduced pressure to obtain solifenacin.

The thus obtained solifenacin was mixed with 12 ml of EtOH, 28 ml of EtOAc and 2.74 g of succinic acid, heated, cooled to 30° C. and then again heated to 50° C. This was kept at 50° C. for 2 hours and then cooled to 0° C. spending 5 hours, and the precipitated crystals were collected by filtration, washed twice with 8 ml of EtOAc and then dried under a reduced pressure to obtain 9.013 g of solifenacin succinate.

The optical isomer content of the solifenacin before salt formation with succinic acid, obtained in Example 1A is shown in Table 1 as the percentage content when solifenacin is defined as 100%. Also, measured data of the determination of the composition concerning compound A, compound B and compound C of the solifenacin before salt formation with succinic acid, obtained in Example 1A is shown in FIG. 3.

Example 1B

A 2.00 g portion of (S)-1-phenyl-1,2,3,4-tetrahydroisoquinoline and 0.48 g of triethylamine were dissolved in 20 ml of toluene, 1.42 g of triphosgene was gradually added thereto, and this was stirred at room temperature for 2 hours. A 0.60 g portion of triethylamine was further added to this reaction solution and stirred overnight. A 10 ml portion of methanol and 20 ml of water were added to this reaction solution, and the water layer was separated. The organic layer was washed with 20 ml of water, and the thus obtained organic layer was concentrated under a reduced pressure, thereby obtaining an oily substance.

A 1.46 g of (R)-quinuclidin-3-ol was dissolved in 15 ml of toluene, 0.46 g of sodium hydride was added thereto under reflux, a solution prepared by dissolving the oily substance obtained in the above in 10 ml of toluene was gradually added dropwise thereto, and this was refluxed overnight to confirm that solifenacin was formed.

Example 2

A mixture of 3.47 g of potassium carbonate and 15 ml of water was added to 5.00 g of (RS)-1-phenyl-1,2,3,4-tetrahydroisoquinoline and 25 ml of toluene, this was cooled to 15° C., 2.72 g of ethyl chloroformate was added dropwise thereto, and this was stirred at 25° C. for 1 hour. The water layer was separated, the organic layer was washed with 15 ml of water, and the solvent was evaporated under a reduced pressure.

A 67 ml portion of toluene, 3 ml of DMF, 3.65 g of (R)-quinuclidin-3-ol and 0.33 g of sodium ethoxide were added to the thus obtained residue and heated for 8 hours while evaporating the solvent. The reaction liquid was cooled, washed by adding 20 ml of toluene and 17 ml of water and again washed with 17 ml of water, and then the organic layer was extracted with a mixture of 3.25 g of concentrated hydrochloric acid and 18 ml of water. 34 ml of EtOAc, and a mixture of 5.28 g of potassium carbonate and 14 ml of water were added to the thus obtained water layer, and the thus obtained organic layer was washed with 7 ml of water, and then the solvent was evaporated under a reduced pressure, thereby obtaining (1RS)-1-phenyl-1,2,3,4-tetrahydroisoquinoline-2-carboxylic acid (3R)-quinuclidin-3-yl ester.

A 6 ml portion of EtOH, 14 ml of EtOAc and 1.30 g of succinic acid were added to the thus obtained (1RS)-1-phenyl-1,2,3,4-tetrahydroisoquinoline-2-carboxylic acid (3R)-quinuclidin-3-yl ester, dissolved by heating and cooled to 50° C., and then 0.003 g of seed crystal of solifenacin succinate produced in the same manner as in Example 1A was added thereto. This mixture was cooled to 30° C., and then again heated to 50° C. This was kept at 50° C. for 2 hours and then cooled to 0° C. spending 5 hours, and the precipitated crystals were collected by filtration, washed twice with 10 ml of EtOAc and then dried under a reduced pressure to obtain 2.855 g of solifenacin succinate as colorless crystals.

In addition, the filtrate after collecting the precipitated crystals by filtration was concentrated under a reduced pressure, and the residue was mixed with 10 ml of toluene and again concentrated under a reduced pressure. A 20 ml portion of toluene was added to this residue, a mixture of 5.00 g of potassium carbonate and 10 ml of water was added thereto, and the thus obtained organic layer was washed with 10 ml of water and concentrated under a reduced pressure. The residue was mixed with 30 ml of toluene and 1.91 g of potassium tert-butoxide, stirred at 100° C. for 5 hours, cooled and then washed twice with 15 ml of water, and the thus obtained organic layer was concentrated under a reduced pressure. This was mixed with 5 ml of EtOH, 11 ml of EtOAc and 1.11 g of succinic acid, dissolved by heating and cooled to 40° C., and then 0.002 g of seed crystal of solifenacin succinate produced in the same manner as in Example 1A was added thereto. This mixture was cooled to 0° C., and the precipitated crystals were collected by filtration, washed with 10 ml of EtOAc and then dried under a reduced pressure to obtain 1.263 g of solifenacin succinate as colorless crystals.

The optical isomer content of the solifenacin succinate obtained in Example 2 is shown in Table 1 as the percentage content when solifenacin is defined as 100%. Also, measured data of the determination of the composition concerning compound A, compound B and compound C of the solifenacin obtained in Example 2 is shown in FIG. 4.

TABLE 1

|  | Example 1A | Example 2 | Reference Example 1 | Reference Example 2 |
| --- | --- | --- | --- | --- |
| Compound A | 0.07 | 0.27 | 7.35 | 4.51 |
| Compound B | 0.74 | 0.11 | 1.70 | 2.33 |
| Compound C | ND | ND | 0.04 | 0.14 |

In this connection, the "ND" in the table means detection limit or less and shows about 0.005% or less.

Example 3

In 100 ml of chloroform and in the presence of 16 g of triethylamine and 0.1 g of 4-dimethylaminopyridine, 12.8 g of ethyl chloroformate was added to 10.0 g of (R)-quinuclidin-3-ol at 10° C. This was heated to 20° C., stirred for 2 hours and mixed with 50 ml of water, the thus obtained organic layer was washed with 50 ml of water, and then the organic layer was concentrated under a reduced pressure and dried in vacuo to obtain 15.49 g of a oily substance. By purifying this oily substance by a silica gel column chromatography, 7.24 g of ethyl (R)-quinuclidin-3-yl carbonate was obtained ($^1$H-NMR (DMSO-$d_6$, tetramethylsilane internal standard): δ 1.21 (3H, t, J=7.2 Hz), 1.26-1.37 (1H, m), 1.42-1.53 (1H, m), 1.55-1.70 (2H, m), 1.91-1.98 (1H, m), 2.48-2.76 (5H, m), 3.06-3.17 (1H, m), 4.11 (2H, q, J=7.2 Hz), 4.56-4.64 (1H, m), mass spectrum: m/z=200 [M+H]$^+$ (FAB)).

In a mixture of 10 ml of toluene and 0.5 ml of DMF and in the presence of 0.21 g of sodium ethoxide, 1.00 g of ethyl (R)-quinuclidin-3-yl carbonate and 1.05 g of (S)-1-phenyl-1,2,3,4-tetrahydroisoquinoline were stirred for 7 hours while evaporating the solvent, 20 ml of toluene and 20 ml of water were added thereto, and the thus obtained organic layer was washed with 20 ml of water and then mixed with 15 ml of 1 M hydrochloric acid aqueous solution. A 30 ml portion of EtOAc and 1 M sodium hydroxide aqueous solution were added to the obtained water layer. The thus obtained organic layer was dried with sodium sulfate, concentrated under a reduced pressure and then dried, and the thus obtained solid was purified by a silica gel column chromatography to obtain 0.22 g of solifenacin.

$^1$H-NMR (DMSO-$d_6$, tetramethylsilane internal standard, 80° C.): δ 1.25-1.38 (1H, m), 1.41-1.53 (1H, m), 1.53-1.65 (1H, m), 1.66-1.77 (1H, m), 1.87-1.96 (1H, m), 2.40-2.96 (7H, m), 3.00-3.15 (1H, m), 3.33-3.45 (1H, m), 3.82-3.92 (1H, m), 4.62-4.69 (1H, m), 6.26 (1H, s), 7.12-7.33 (9H, m).

Mass spectrum: m/z=363 [M +H]$^+$ (FAB)

Example 4A

A 15.00 g portion of (S)-1-phenyl-1,2,3,4-tetrahydroisoquinoline and 9.22 g of isopropyl chloroformate were added to a mixture of 75 ml of toluene, 10.43 g of potassium carbonate and 45 ml of water and stirred at 20° C. for 2 hours, and then the organic layer was washed with 50 ml of water. The thus obtained organic layer was concentrated under a reduced pressure and then dried to obtain 21.71 g of (S)-1-phenyl-1,2,3,4-tetrahydroisoquinoline-2-carboxylic acid propan-2-yl ester ($^1$H-NMR (DMSO-$d_6$, tetramethylsilane internal standard, 80° C.): δ 1.18 (3H, d, J=6.4 Hz), 1.22 (3H, d, J=6.4 Hz), 2.73-2.93 (2H, m), 3.25-3.34 (1H, m), 3.83-3.92 (1H, m), 4.80-4.91 (1H, m), 6.22 (1H, s), 7.06-7.33 (9H, m), mass spectrum: m/z=296 [M +H]$^+$ (FAB)).

In a mixture of sodium isopropoxide prepared from 0.20 g of 2-propanol and 0.08 g of metallic sodium with 20 ml of toluene and 2.5 ml of DMF, 2.58 g of (R)-quinuclidin-3-ol was allowed to react with 5.00 g of (S)-1-phenyl-1,2,3,4-tetrahydroisoquinoline-2-carboxylic acid propan-2-yl ester for 8 hours while evaporating the solvent, thereby obtaining 3.97 g of a solifenacin-containing composition.

A compound in which isopropyl or the like lower alkyl is added to the 2-position of quinuclidine in solifenacin, like the case found in Reference Example 2, Reference Example 3 and Reference Example 4, was not contained in the solifenacin-containing composition obtained in Example 4A.

In this connection, determination of the composition of this composition was carried out by the following method.

A 0.01 g portion of the solifenacin-containing composition obtained in the aforementioned Example 4A was dissolved in a solution which had been prepared by dissolving 6.1 g of sodium perchlorate in, adjusting this to 1000 ml and adjusting its pH to 2.0 by adding perchloric acid (to be referred to as liquid Q hereinafter), and the total volume was adjusted to 10 ml to be used as a sample solution. A 10 μl portion of this sample solution was tested by a liquid chromatography under the following conditions, and the peak area was measured by an automatic analysis method.

<Test Conditions>
Detector: ultraviolet absorptiometer (measuring wavelength: 210 nm)
Column: Develosil ODS-UG-5 (150 mm×4.6 mm ID, mfd. by Nomura Chemical)
Column temperature: 40° C.
Mobile phase: liquid Q
Flow rate: about 1 ml/min Example 4B A 10.00 g portion of (S)-1-phenyl-1,2,3,4-tetrahydroisoquinoline and 10.41 g of tert-butyl dicarbonate were added to a mixture of 50 ml of toluene, 6.95 g of potassium carbonate and 30 ml of water and stirred at 20° C. overnight, and then the organic layer was washed with 30 ml of water. The thus obtained organic layer was concentrated under a reduced pressure and then dried to obtain 14.59 g of (S)-1-phenyl-1,2,3,4-tetrahydroisoquinoline-2-carboxylic acid 2-methylpropan-2-yl ester ($^1$H-NMR (DMSO-$d_6$, tetramethylsilane internal standard, 80° C.): δ 1.39 (9H, s), 2.72-2.91 (2H, m), 3.28-3.32 (1H, m), 3.80-3.89 (1H, m), 6.18 (1H, s), 7.07-7.33 (9H, m), mass spectrum: m/z=310 [M +H]$^+$ (FAB)).

In a mixture of 0.38 g of sodium tert-butoxide, 60 ml of toluene and 3 ml of DMF, 2.96 g of (R)-quinuclidin-3-ol was allowed to react with 6.00 g of (S)-1-phenyl-1,2,3,4-tetrahydroisoquinoline-2-carboxylic acid 2-methylpropan-2-yl ester for 8 hours while evaporating the solvent, thereby obtaining 0.274 g of a solifenacin-containing composition.

A compound in which tert-butyl or the like lower alkyl is added to the 2-position of quinuclidine in solifenacin, like the case found in Reference Example 2, Reference Example 3 and Reference Example 4, was not contained in the solifenacin-containing composition obtained in Example 4B.

In this connection, determination of the composition of this composition was carried out in accordance with the determination method of the composition obtained in the aforementioned Example 4A.

TABLE 2

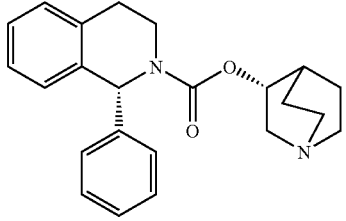

| | R$^A$ | Percentage content of each compound |
|---|---|---|
| Reference Example 2 | ethyl (compound D) | 0.67 |
| Reference Example 3 | methyl (compound E) | 0.20 |
| Reference Example 4 | benzyl (compound F) | 0.07 |
| Example 4A | isopropyl | ND |
| Example 4B | tert-butyl | ND |

In this connection, the "ND" in the table means detection limit or less and shows about 0.005% or less.

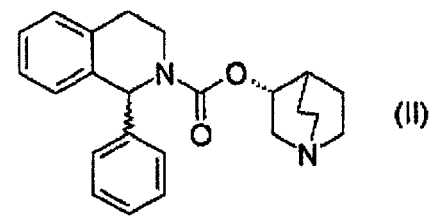

The invention claimed is:

1. A method for producing solifenacin or a pharmaceutically acceptable salt thereof, which is a method for producing solifenacin succinate, which comprises allowing succinic acid to react with a compound represented by a formula (II)

(II)

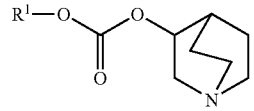

in the formula, stereochemistry of the 1-position of phenyl-substituted tetrahydroisoquinoline is a mixture of (R)-form and (S)-form.

2. A method for producing solifenacin or a pharmaceutically acceptable salt thereof, which comprises allowing a compound represented by a formula (III)

(III)

R$^1$—O—C(=O)—O—[quinuclidinyl]

in the formula, R$^1$ represents a lower alkyl which may be substituted, and (S)-1-phenyl-1,2,3,4-tetrahydroisoquinoline or a salt thereof to undergo condensation.

3. A method for producing solifenacin or a pharmaceutically acceptable salt thereof, which comprises allowing a compound represented by a formula (IV)

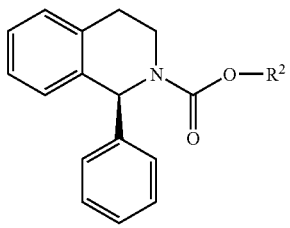

(IV)

in the formula, $R^2$ represents a secondary lower alkyl or a tertiary lower alkyl, which may be respectively substituted, and (R)-quinuclidin-3-ol to undergo reaction in the presence of an alkali metal lower alkoxide.

4. The production method described in claim 3, wherein the lower alkoxide of the alkali metal lower alkoxide is a secondary lower alkoxide or a tertiary lower alkoxide.

* * * * *

UNITED STATES PATENT AND TRADEMARK OFFICE
CERTIFICATE OF CORRECTION

PATENT NO. : 7,829,715 B2
APPLICATION NO. : 11/587826
DATED : November 9, 2010
INVENTOR(S) : Masatoshi Inakoshi and Yusuke Ishii It is certified that error appears in the above-identified patent and that said Letters Patent is hereby corrected as shown below:

Col. 3, Line 55-64
Please amend the compound of formula (II) at column 3 as follows:

Delete " 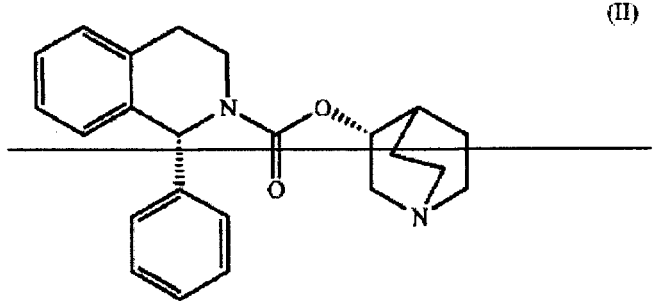 "

Should read 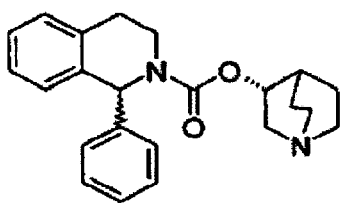

Signed and Sealed this
Twentieth Day of September, 2011

David J. Kappos
*Director of the United States Patent and Trademark Office*

Col. 6, Line 1-20
Please amend the reaction scheme for "(2) Production Method (2)" at column 6 as follows:
Delete "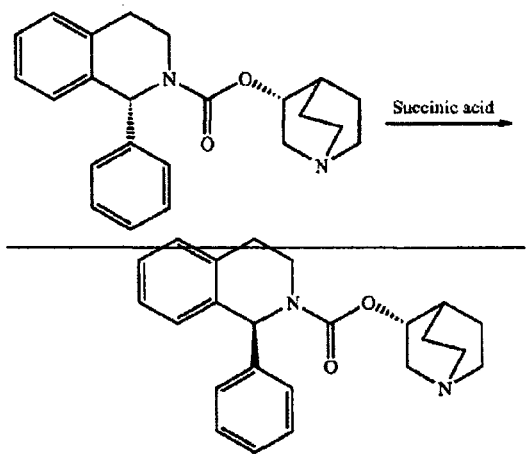"
Should read 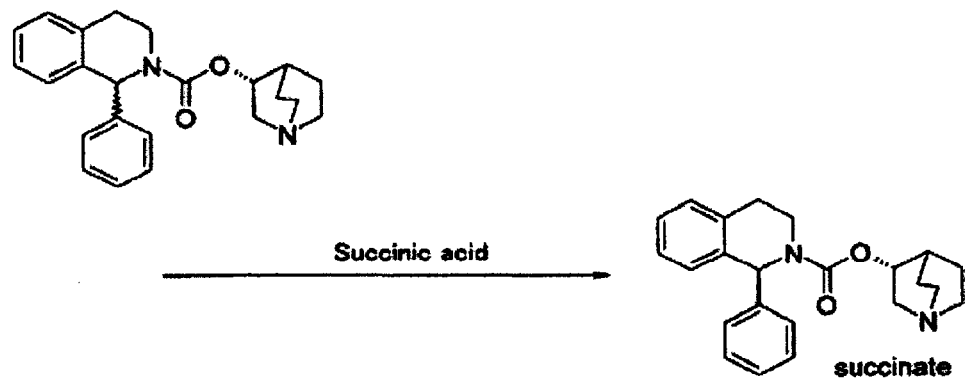
Col. 11, Line 40-45
Please amend the compounds of formulae A, B, and F in the reaction scheme at columns 11-13 as follows:
Delete "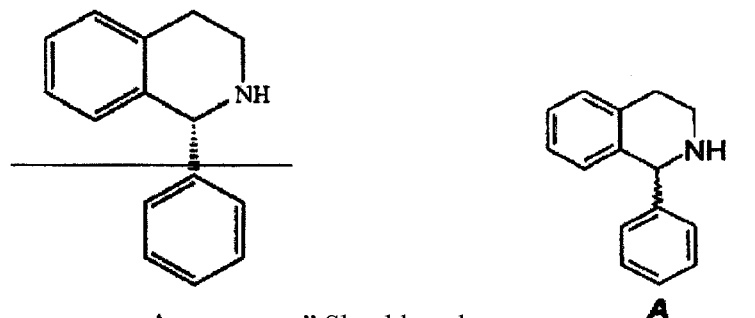"

CERTIFICATE OF CORRECTION (continued)
U.S. Pat. No. 7,829,715 B2

Col. 12, Line 40-45

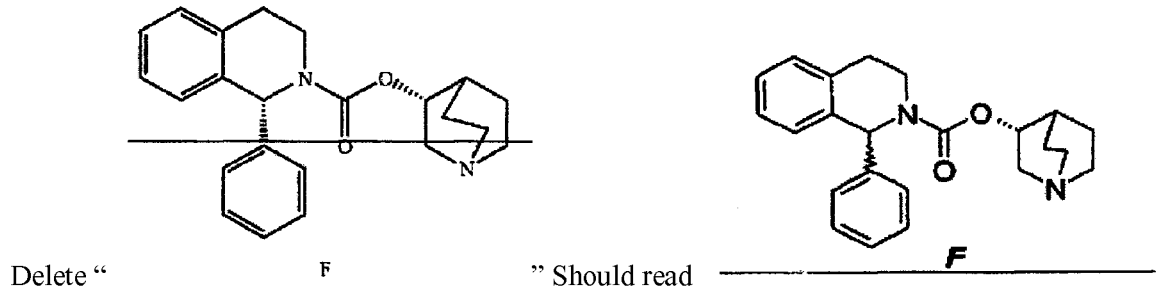

Delete " F " Should read ———— F ————

Col. 13, Line 1-15

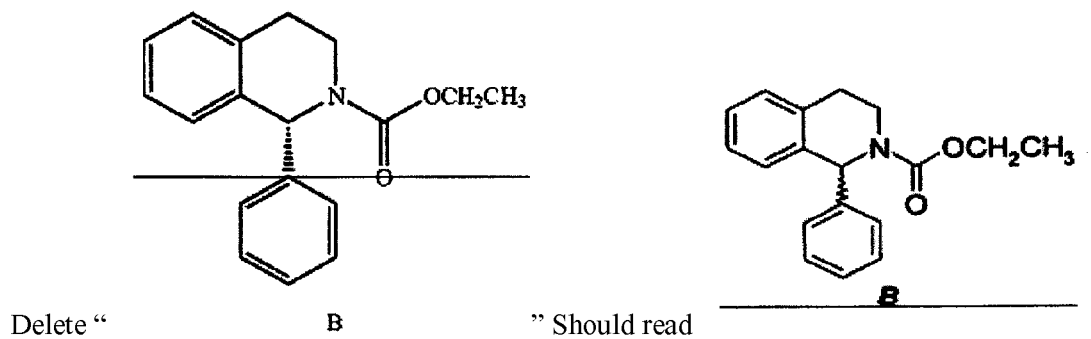

Delete " B " Should read ———— B ————

Please amend the compound of formula (II) in claim 1 at col. 22 as follows:

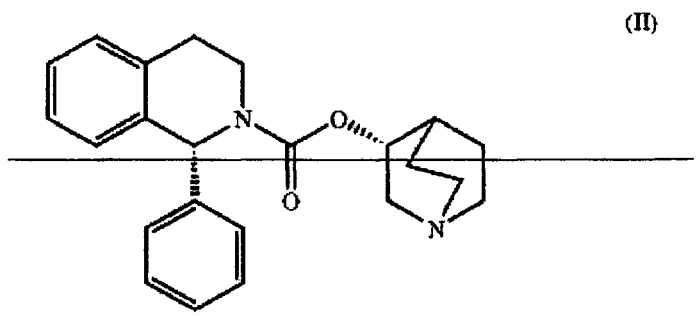

Should read